(12) United States Patent
White

(10) Patent No.: US 10,188,611 B2
(45) Date of Patent: Jan. 29, 2019

(54) STABLE LIQUID FILLED HARD CAPSULE COMPRISING BETA-HYDROXY-BETA METHYLBUTYRIC ACID

(71) Applicant: Capsugel Belgium NV, Bornem (BE)

(72) Inventor: Tyler Oswald White, Greenwood, SC (US)

(73) Assignee: Capsugel Belguim NV, Bornem (BE)

( * ) Notice: Subject to any disclaimer, the term of this patent is extended or adjusted under 35 U.S.C. 154(b) by 0 days.

(21) Appl. No.: 15/036,162

(22) PCT Filed: Dec. 11, 2014

(86) PCT No.: PCT/US2014/069831
§ 371 (c)(1),
(2) Date: May 12, 2016

(87) PCT Pub. No.: WO2015/094925
PCT Pub. Date: Jun. 25, 2015

(65) Prior Publication Data
US 2016/0296475 A1    Oct. 13, 2016

Related U.S. Application Data

(60) Provisional application No. 61/917,692, filed on Dec. 18, 2013.

(51) Int. Cl.
*A61K 9/48* (2006.01)
*A61K 31/19* (2006.01)

(52) U.S. Cl.
CPC .......... *A61K 9/4808* (2013.01); *A61K 9/4816* (2013.01); *A61K 9/4833* (2013.01); *A61K 9/4858* (2013.01); *A61K 9/4866* (2013.01); *A61K 31/19* (2013.01)

(58) Field of Classification Search
None
See application file for complete search history.

(56) References Cited

U.S. PATENT DOCUMENTS

| | | | |
|---|---|---|---|
| 5,919,481 A | 7/1999 | Cody et al. | |
| 6,294,192 B1 | 9/2001 | Patel et al. | |
| 6,451,339 B2 | 9/2002 | Patel et al. | |
| 8,217,077 B2 | 7/2012 | Baxter et al. | |
| 2003/0129295 A1* | 7/2003 | Richardson | A23K 50/10 426/635 |
| 2007/0059355 A1* | 3/2007 | Madit | A61K 31/205 424/451 |
| 2012/0053240 A1* | 3/2012 | Rathmacher | A61K 31/19 514/557 |

FOREIGN PATENT DOCUMENTS

| | | |
|---|---|---|
| EP | 1 158 959 | 12/2001 |
| EP | 1762232 | * 3/2007 |
| WO | WO 01/12155 | 2/2001 |
| WO | WO 2010072892 | * 12/2008 |
| WO | WO 2011/075741 | * 6/2011 |

OTHER PUBLICATIONS

Nagata "Advantages to HPMC Capsules: A New Generation's" 2008.*
International Search Report from related International Application No. PCT/US2014/069831, dated Mar. 18, 2015 (3 pages).
Written Opinion from related International Application No. PCT/US2014/069831, dated Mar. 18, 2015 (5 pages).
Stout et al., "Effect of calcium β-hydroxy-β-methylbutrate (CaHMB) with and without resistance training in men and woman 65+ yrs: A randomized, double-blind pilot trial," *Experimental Gerontology*, 48(11): 1303-1310, Aug. 24, 2013.

* cited by examiner

*Primary Examiner* — Robert A Wax
*Assistant Examiner* — Danah Al-Awadi
(74) *Attorney, Agent, or Firm* — Klarquist Sparkman, LLP

(57) ABSTRACT

The present disclosure relates to liquid filled hard capsules comprising hydroxypropyl methyl cellulose, pullulan, or mixtures thereof comprising a liquid fill of an effective amount of beta-hydroxy-beta-methylbutyric acid (HMB free acid) in liquid form and at least on excipient selected from quaternary ammonium salts, amino acids, amino acid derivatives, monosaccharides, disaccharides, and mixtures thereof.

19 Claims, 1 Drawing Sheet

STABLE LIQUID FILLED HARD CAPSULE COMPRISING BETA-HYDROXY-BETA METHYLBUTYRIC ACID

CROSS REFERENCE TO RELATED APPLICATIONS

This is the U.S. National Stage of International Application No. PCT/US2014/069831, filed Dec. 11, 2014, which was published in English under PCT Article 21(2), which in turn claims the benefit of the earlier filing date of U.S. provisional application No. 61/917,692, filed on Dec. 18, 2013, each of which is incorporated herein by reference in its entirety.

FIELD

The present disclosure relates to a stable liquid filled non-gelatin hard capsule unit dose form comprising beta-hydroxy-beta-methylbutyric free acid and at least one excipient in a liquid fill.

BACKGROUND

Hard capsules are widely used in the pharmaceutical field as oral dosage forms for administration to humans and animals of, e.g., pharmaceuticals, veterinary products, and food and dietary supplements. Hard capsules have advantages compared to other conventional dosage forms including better patient compliance, greater flexibility in dosage form design, and less expensive manufacturing processes. Pharmaceutical capsules are conventionally divided into soft shell capsules (hereinafter soft capsules) and hard shell capsules (hereinafter hard capsules).

For many pharmaceutical and/or health and nutrition applications, e.g., when active ingredients are to be administered, it is often desirable that the substances to be encapsulated are pre-mixed with at least one excipient to form a composition which is then filled into capsules. The resulting combination of active ingredient with at least one excipient must be compatible with the capsule shell in that it must not affect the capsule shell stability after filling. Typical compatibility issues that may arise are impairment of the mechanical properties of the capsule shells resulting, e.g., in leaks and/or softening of the shells and/or impairment of the chemical properties of the capsule shells, including but not limited to modification of the capsule shell dissolution profile.

Hard capsules are often commercially preferable over soft capsules since they have a simpler manufacturing process (i.e., hard capsule shells are manufactured separately and empty while the active ingredient and formulation fill can be formulated in a separate step), more flexibility in the filling step(s), and easier equipment operability as compared to soft capsules. For these reasons, it would be desirable that a liquid fill be compatible with hard capsules. Hard capsule shells may be manufactured with a variety of polymeric substances such as gelatin, hydroxypropyl methyl cellulose (HPMC), and pullulan, as well as mixtures thereof. The liquid fill must be compatible with the hard capsule shell polymeric substance selected, and not every liquid fill is compatible with every hard shell capsule shell.

While gelatin capsules are readily available and are often utilized, gelatin capsules containing certain moisture levels may lose plasticity and may show serious deterioration in impact resistance. A desire for animal-product free vegetarian capsules has resulted in an interest in non-gelatin based hard capsules. Plant-based hard capsules, such as HPMC capsules and pullulan capsules, prepared without gelatin, are of particular interest. Additionally, certain active ingredients, particularly liquid fills, interact deleteriously with gelatin while cellulose derivatives such as HPMC may be less reactive with certain active ingredients and with certain liquid fills, particularly hygroscopic or reactive active ingredients.

HPMC capsules include VCAPS® hypromellose capsules and VCAPS® Plus hypromellose capsules available from Capsugel. HPMC capsules have low moisture content, are vegetarian, and have low cross-linking. Pullulan capsules include PLANTCAPS® capsules available from Capsugel.

It is also desirable that the fill be liquid, since this facilitates capsule filling step as well as gastro-intestinal release and absorption of the substance(s) after capsule shell disintegration. In particular, for a liquid active ingredient, a liquid fill is desirable if it is stable in the capsule shell chosen.

It is also desirable that the liquid fill be not visually opaque or milky since this has been linked to lower patient compliance.

It is also desirable that the liquid fill and/or the excipients chosen be compatible with the active ingredient(s) and/or substances intended to be pre-mixed with it. Typically, instability can result in oxidation and/or hydrolysis over time of the active ingredients mixed in the liquid fill.

The carboxylic acid, β-hydroxy-β-methylbutyric acid or HMB, is an active metabolite of the branched-chain amino acid leucine. Endogenous production in humans is in small amounts (Nissen S L, Abumrad N N, Nutritional role of the leucine metabolite β-hydroxy-β-methylbutyrate (HMB). *J Nutr Biochem.* 1997; 8:300-11). Activity of HMB in humans and other mammals is reported to include reducing blood cholesterol and low-density lipoprotein levels, promoting nitrogen retention, increasing lean tissue development, enhancing the immune response, combating disease associated wasting, and increasing the aerobic capacity of muscle without increase in muscle mass, among other effects. See, e.g., U.S. Patent Application Publication No. 2012/0053240; Hasselgren P-O, β-hydroxy-β-methylbutyrate (HMB) and prevention of muscle wasting, *Metabolism Clinical and Experimental* (2013), in press. In its acid form, the compound is called 3-hydroxy-3-methylbutyric acid, β-hydroxy-β-methylbutyric acid, or β-hydroxy-isovalaryic acid, and can be designated "HMB free acid." The structural formula for HMB free acid is $(CH_3)_2C(OH)CH_2COOH$.

U.S. Patent Application Publication No. 2012/0053240 to Rathmacher et al. discloses methods of administering HMB free acid, and solids, tablets, capsules, and liquids generally, and discloses that HMB free acid because it is a liquid is much more difficult to deliver or incorporate into products, particularly unit dosage forms. Further, the HMB free acid has the impurity 3,3-dimethyl acrylic acid with a very off flavor which is difficult to mask. For these reasons, nearly all dosage forms to date have utilized the calcium salt in crystalline powder form, despite the lowered biological effectiveness of the salt compared to the free acid. Biological testing has been performed with the salt form for muscle quality compared to placebo (*Experimental Gerontology* 48 (2013) 1303-1310). Because HMB free acid is a liquid at room temperature, a tablet form containing HMB free acid would not be physically compatible and thus could not be readily manufactured. While administration of HMB free acid in the form of gels or as an additive in nutritional food products (including liquids) is possible, such administration is less palatable and less convenient for the patient compared to capsules, leading to lower patient compliance. Pure HMB free acid in gel form is not compatible with hard capsules. A stable hard capsule unit dosage form of the HMB free acid is therefore desirable and would result in greater patient compliance and a reduced need for taste masking agents. Lack of such a hard capsule unit dosage form has hindered testing of HMB free acid.

U.S. Pat. No. 8,217,077 to Baxter et al. discloses methods of stimulating new protein synthesis in patients affected by disease-associated wasting conditions by treatment with β-hydroxy-β-methylbutyric acid formulated as a solid, crystalline salt form into capsules or dissolved in water. Baxter did not distinguish between the crystalline salt form and the liquid free acid of HMB.

U.S. Pat. Nos. 6,294,192 and 6,451,339, and European Patent Applications EP1158959A and EP1210063A disclose compositions comprising a liquid carrier for the administration of hydrophilic or hydrophobic active agents. Generally, the carriers are comprised of one hydrophilic surfactant and one hydrophobic surfactant, the former being in greater amount. These documents disclose huge lists of ingredients that can be variably combined to obtain equally effective carriers for liquid fills. No data are provided to infer stability of hard capsule shells after filling with liquid fills, or deleterious effects of liquid active ingredients, on hard capsule integrity.

U.S. Pat. No. 5,919,481 discloses carriers for the administration of substances (including hydrophobic ones) prone to human abuse. The aim of these carriers is to reduce the risk of drug abuse. Accordingly, these carriers must be highly viscous at room temperature so that they cannot be freely removed with a syringe. Additionally, no data are provided regarding stability of any hard capsule shells in case these carriers had to be filled into hard capsules.

Thus, an object of the present disclosure is to provide a physically stable, liquid filled hard capsule comprising HMB free acid and at least one excipient. Further objects are to provide a liquid filled hard capsule that has a liquid fill which is clear at room temperature and that is compatible with the substances that are mixed with it before being filled into hard capsule shells, in particular to provide a stable, liquid filled hard capsule containing the active ingredient beta-hydroxy-beta-methylbutyric acid, either alone or in combination with other active ingredient(s).

SUMMARY

The above and other objects are achieved by a composition particularly suitable for filling into hard HPMC capsules, said composition comprising a transparent liquid fill comprising HMB free acid and one or more additional substances.

The above and other objects are also achieved by the process for manufacturing a hard capsule, said method comprising the step of filling a hard HPMC capsule shell with a transparent liquid fill comprising HMB free acid.

The above and other objects are also achieved by the use of a stable, liquid filled hard capsule for the administration of HMB free acid to a human or an animal.

DESCRIPTION OF THE DRAWING

FIG. 1 is a photograph of the HMB free acid liquid filled HPMC capsule made according to Example 7 after six months' storage at room temperature.

DETAILED DESCRIPTION

Embodiments according to the disclosure include a liquid filled hard capsule comprising a hard capsule shell comprising hydroxypropyl methyl cellulose, pullulan, or mixtures thereof; a liquid fill inside the hard capsule shell comprising an effective amount of beta-hydroxy-beta-methylbutyric acid (HMB free acid) in liquid form and at least one excipient selected from quaternary ammonium salts, amino acids, amino acid derivatives, monosaccharides, disaccharides, and mixtures thereof, wherein said excipient is present from about 30% w/w to about 60% w/w, particularly from about 40% to about 50% w/w, of the liquid fill; wherein the liquid filled hard capsule is physically stable.

In certain embodiments, the at least one excipient is selected from the group consisting of choline chloride, L-carnitine base, beta-alanine, and mixtures thereof; specifically choline chloride.

In certain embodiments, the at least one excipient consists of a quaternary ammonium salt selected from the group consisting of L-carnitine base, L-carnitine HCl, acetyl-L-carnitine, L-carnitine tartrate, glycine propionyl-L-carnitine, and mixtures thereof.

In certain embodiments, the at least one excipient consists of an amino acid selected from the group consisting of L-arginine ethyl ester HCl, beta alanine, L-isoleucine, HCl, L-leucine ethyl ester HCl, valine ethyl ester HCl, L-arginine ethyl ester HCl, and mixtures thereof.

In certain embodiments, the at least one excipient consists of a saccharide selected from the group consisting of fructose, sucrose, D-ribose, and mixtures thereof.

In certain embodiments, the least one excipient is present in an amount from about 35% w/w to about 40% w/w, particularly about 38% w/w, of the liquid fill.

Optionally, embodiments according to the disclosure further comprise at least one of a colorant, a surfactant, a viscosity modifying agent, and mixtures thereof.

In certain embodiments, the liquid filled hard capsules are stable under conditions of 40° C./75% relative humidity for at least three months, more preferably are stable under conditions of 40° C./75% relative humidity for at least six months.

Embodiments according to the disclosure include processes for manufacturing a liquid filled hard capsule, comprising filling a hard capsule shell comprising hydroxypropyl methyl cellulose, pullulan, or mixtures thereof; having a cap and a body with a liquid fill comprising an effective amount of beta-hydroxy-beta-methylbutyric acid (HMB free acid) in liquid form and at least one excipient selected from quaternary ammonium salts, amino acids, amino acid derivatives, monosaccharides, disaccharides, and mixtures thereof, wherein said excipient is present from about 30% w/w to about 60% w/w, particularly from about 40% to about 50% w/w, of the liquid fill; wherein the liquid filled hard capsule is physically stable and sealing or banding the liquid filled hard capsule where the cap and the body overlap.

Embodiments according to the invention include methods of using a liquid filled hard capsule as defined in any of the preceding claims for the administration of HMB free acid to a human or an animal.

Unless otherwise indicated, hard capsules according to the instant disclosure are commercially available hard capsules intended for oral administration to a human or animal being. Such hard capsules are generally manufactured from polymers by using a dip molding process and equipment. In this process, pin molds are dipped into an aqueous-based film forming composition. By subsequently gelling the composition adhered on the pins a film is formed. The film is then dried, stripped off the pins and cut to a desired length. Thus, capsules caps and bodies are obtained. Such two parts are then co-axially, telescopically joined so as to form a capsule shell. Normally, caps and bodies have a side wall, an open end and a closed end. The length of the side wall of each of said parts is generally greater than the capsule diameter. The capsule caps and bodies are telescopically joined together so as to make their side walls partially overlap and obtain a hard capsule shell. "Partially overlap" also encompasses an embodiment wherein the side walls of caps and bodies have substantially the same length so that, when a cap and a body are telescopically joined, the side wall of said cap encases the entire side wall of said body. Unless otherwise indicated, "capsule" refers to filled capsule shells whereas "shell" specifically refers to an empty capsule.

Hard capsules and shells according to certain embodiments are hard capsules made from hydroxypropyl methyl cellulose, pullulan, and mixtures thereof. Preferably, the capsule shells are made from cellulosic polymers such as hydroxypropyl methyl cellulose (HPMC). These shells are typically obtained by dip molding processes from a water solution containing hydroxypropyl methyl cellulose as shell film forming polymer and other optional ingredients known to skilled persons. In certain embodiments, the capsule shell comprises HPMC from about 85% to about 100%, preferably from about 92% to about 97%, HPMC by w/w of the empty capsule. In certain embodiments, the capsule shell comprises pullulan from about 80% to about 95%, preferably from about 87% to 90%, pullulan by w/w of the empty capsule.

Since the hard capsule shells of the instant disclosure are filled with substances in liquid form, it is intended that if desired the hard capsules may be sealed or banded according to conventional techniques, either by hand or via automatic banding or sealing equipment.

Unless otherwise indicated, references to compatibility of the liquid fill with HPMC hard capsule shells, or hard pullulan capsule shells, or stability of a hard capsule shell, preferably means that the liquid fill, after filling into a hard capsule shell, does not impact the physical stability of the capsule, i.e., the capsules remain intact and rigid without leaking, deformation, discoloration, and/or excessive softening or brittleness when observed over the indicated time period. Physical stability or physically stable relates to at least mechanical stability of said shell, more preferably to both mechanical and chemical stability of said shell. Mechanical stability can for example be evaluated based on maintenance of hardness of the shell and absence of leaks. Chemical stability can for example be evaluated based on maintenance of an appropriate dissolution profile of an encapsulated substance (for this latter aspect, reference can be made to e.g. USP-32 substance monographs).

In one embodiment, the liquid fill, after filling into a hard capsule shell as defined above, does not impact mechanical and chemical stability, beyond an acceptable level. In one embodiment, an acceptable level is a commercially acceptable level. In one embodiment, a commercially acceptable level is a level recognised by a skilled person in the field of hard capsules, preferably liquid filled hard capsules, as a satisfactory level to commercialize the carrier filled hard capsules with acceptable manufacturing costs.

In one embodiment, the liquid fill does not affect the physical stability of a hard capsule shell (mechanical or chemical) beyond an acceptable level if, when filling a batch of preferably at least 50 hard capsule shells with said liquid fill and subjecting the filled capsules to a mechanical robustness test (e.g. tube test) at a specified shell loss on drying (LOD), 0% of the capsules in said batch fail at a shell water content comprised between about 2% and about 6% LOD. Such "mechanical robustness test" demonstrates alterations in the mechanical properties of the capsule due to interactions between the fill and the shell and to evaluate the potential tendency for brittleness or softening when filled and stored at various relative humidity conditions and temperatures.

General methods for testing mechanical robustness and capsule stability are disclosed in D. Cadé and N. Madit, "Liquid Filling in Hard Gelatin Capsules—Preliminary Steps", *Bulletin Technique Gattefossé*, 1996.

In one embodiment, chemical stability of a hard capsule shell is achieved to an acceptable level if, when filling a batch of preferably at least 6 hard capsule shells with said liquid fill, none of the filled capsules in said batch release less than about 80% of the filled active ingredient(s) at 45 minutes in simulated gastric fluid (pepsin) after 6 months at storage conditions of 40° C. and 75% RH.

HMB free acid is typically used as an active ingredient or dietary supplement in humans or other mammals. An effective amount for supplementation of HMB is in the dosage range of from about 1 g to about 3 g daily for the purpose of reducing muscle mass losses over time (anti-catabolic effect). The effective amount for a dose for a human or other mammal is known and can be adjusted as needed for body mass, health, number of administration times, and other variables. See Wilson, J. M., et al., *Br. J. of Nutrition*, Vol. 110, pp 538-544 (2013).

In certain embodiments, the liquid fill is clear and transparent by simple visual inspection at 25° C. Transparent as used herein means the % transmittance from 400-700 nm of greater than about 95%, more preferably greater than about 97%.

Unless otherwise indicated, room temperature is preferably about 25° C.

The liquid fill according to certain embodiments means the liquid fill is liquid at room temperature, typically about 700 cPs to about 1000 cPs, particularly about 800 cPs.

The liquid fill prior to filling into a hard capsule can be prepared by simply mixing the ingredients in the desired amounts into appropriate pharmaceutical mixing equipment for fluids and semi-solids.

A skilled person can readily determine by means of routine tests (e.g. spectrophotometry or empirical visual observation) when solutions are obtained. Typically, a solution is obtained when UV-visible absorbance of the composition at 400 nm and 25° C. is within the values about 0 to about 0.05.

Optionally, the liquid fill can further contain an antioxidant, a colorant, a preservative, a surfactant, a viscosity modifying agent, and mixtures thereof. Non-limiting examples of antioxidants include ascorbic acid and preservatives. Non-limiting examples of preservatives are BHA (butyl hydroxyanisole), BHT (butyl hydroxutoluene), and ascorbyl palmitate. Non-limiting examples of a surfactant include polysorbate. Non-limiting examples of viscosity modifying agents include silicon dioxide and HPMC. The other ingredients must maintain the transparent liquid nature of the fill and must not provide deleterious effects on the hard capsule shell.

In one embodiment, the filled hard capsule is made tamper-proof by using appropriate techniques to make the joint permanent. Typically, sealing or banding techniques can be used where these techniques are well-known to any skilled person in the field of hard capsules.

In another aspect, the present disclosure relates to a process for manufacturing a hard capsule as defined herein, said method comprising the step of filling a hard capsule shell with a liquid fill comprising beta-hydroxy-beta-methylbutyric free acid.

Further embodiments and advantages will become apparent to a skilled reader in light of the examples provided below. The following examples are illustrative and are not intended to limit the scope of the disclosure.

"Percent" in the Examples provided is the weight percentage of the total liquid fill weight (w/w). Where utilized, HDPE bottles were sealed via pressure seal lined tamper evident caps. Densities of the liquid fill range from about 1.0 to about 1.3 g/ml. Approximate fill weight ranges and approximate volumes for various capsule sizes are as indicated. Any capsule size may be used suitable for administration to a human or other mammal.

| Capsule Size | Approx. Fill Weight (mg) (Lower) | Approx. Fill Weight (mg) (Upper) | Approx. Fill Volume (ml) |
| --- | --- | --- | --- |
| Size 000 | 1320 | 1500 | 1.2 |
| Size 00 | 864 | 982 | 0.79 |
| Size 0 | 620 | 705 | 0.56 |
| Size 1 | 451 | 513 | 0.41 |
| Size 2 | 347 | 394 | 0.32 |
| Size 3 | 248 | 282 | 0.23 |
| Size 4 | 186 | 212 | 0.17 |

EXAMPLE 1

A formulation of the composition according to Table 1 was prepared with HMB free acid alone.

TABLE 1

| Item # | Ingredient | Percent |
| --- | --- | --- |
| 1 | HMB Free Acid | 100% |
|  | Total | 100% |

Item 1, pure HMB free acid, was heated to 30° C. for encapsulation in an HPMC capsule (VCaps® Plus capsule, size 0) followed by LEMS® automated sealing with a solution of isopropyl alcohol 75%/25% water, and dried at 55° C. for approximately 3 minutes (standard conditions used for all Examples, unless indicated otherwise). Filled capsules were then placed in 200 cc HDPE bottles with 2 grams silica gel desiccant in an accelerated stability chamber at 40° C./75% RH. Noticeable deterioration and softening of the capsule shell occurred after 2 days, indicating that the HMB free acid in its native liquid form was incompatible with the HPMC capsule.

EXAMPLE 2

Pure HMB free acid was filled into gelatin capsules as follows. The HMB free acid was heated to 30° C. for encapsulation in a size 0 gelatin capsule (Licap® capsule from Capsugel) followed by LEMS® automated sealing with a solution of ethanol 50%/50% water heated to 48° C. for three minutes and left to dry at room temperature. Noticeable deterioration and softening of the capsule shell occurred after one day, indicating that the HMB free acid in its native liquid form was incompatible with the gelatin capsules.

EXAMPLE 3

A formulation of the composition according to Table 2 was prepared:

TABLE 2

| Item # | Ingredient | Percent |
| --- | --- | --- |
| 1 | HMB Free Acid | 57% |
| 2 | HPMC | 43% |
|  | Total | 100% |

Items 1 and 2 were added together and stirred for a minimum of 30 minutes at 70° C. using a 3-blade mixer at 200 RPM until dissolution occurred, resulting in a colorless, transparent liquid fill. The temperature was reduced to 30° C. for encapsulation in an HPMC capsule (VCaps® Plus capsule, size 0, 50 capsules) followed by LEMS® automated sealing with a solution of isopropyl alcohol 75%/25% water. The filled capsules were then placed in 200 cc HDPE bottles in an accelerated stability chamber at 40° C./75% RH. Noticeable deterioration and softening of the capsule shell occurred after 3 days.

EXAMPLE 4

A formulation of the composition according to Table 3 was prepared:

TABLE 3

| Item # | Ingredient | Percent |
| --- | --- | --- |
| 1 | HMB Free Acid | 57% |
| 2 | PEG 3350 | 43% |
|  | Total | 100% |

Items 1 and 2 (PEG 3350, polyethylene glycol, average molecular weight 3350 Da) were added together and stirred for a minimum of 30 minutes at 70° C. using a 3-blade mixer at 200 RPM until dissolution occurred. The temperature was reduced to 30° C. for encapsulation in an HPMC capsule (VCaps® Plus capsule, size 0, 50 capsules) followed by LEMS® automated sealing with a solution of isopropyl alcohol 75%/25% water. These were then placed in 200 cc HDPE bottles in an accelerated stability chamber at 40° C./75% RH. Noticeable deterioration and softening of the capsule shell occurred after 3 days.

EXAMPLE 5

A formulation of the composition according to Table 4 was prepared:

TABLE 4

| Item # | Ingredient | Percent |
| --- | --- | --- |
| 1 | HMB Free Acid | 57% |
| 2 | Glycerin | 43% |
|  | Total | 100% |

Items 1 and 2 were added together and stirred for a minimum of 30 minutes at 70° C. using a 3-Blade mixer at 200 RPM, resulting in a colorless, transparent liquid fill. The temperature was reduced to 30° C. for encapsulation in an HPMC capsule (VCaps® Plus capsule, size 0, 50 capsules) followed by LEMS® automated sealing with a solution of isopropyl alcohol 75%/25% water. The filled capsules were then placed in 200 cc HDPE bottles in an accelerated stability chamber at 40° C./75% RH. Noticeable deterioration and softening of the capsule shell occurred after 3 days.

EXAMPLE 6

A formulation of the composition according to Table 5 was prepared:

TABLE 5

| Item # | Ingredient | Percent |
|---|---|---|
| 1 | HMB Free Acid | 57% |
| 2 | L-Carnitine Base | 43% |
| | Total | 100% |

Items 1 and 2 were added together and stirred for a minimum of 30 minutes at 70° C. using a 3-blade mixer at 200 RPM, resulting in a transparent liquid fill. The temperature was reduced to 30° C. for encapsulation in an HPMC capsule (VCaps® Plus capsule, size 0, 50 capsules) followed by LEMS® automated sealing with a solution of isopropyl alcohol 75%/25% water. The filled capsules were then placed in 200 cc HDPE bottles in an accelerated stability chamber at 40° C./75% RH. Capsules remained stable following 6 months exposure at accelerated conditions.

EXAMPLE 7

A formulation of the composition according to Table 6 was prepared:

TABLE 6

| Item # | Ingredient | Percent |
|---|---|---|
| 1 | HMB Free Acid | 60% |
| 2 | Choline Chloride | 40% |
| | Total | 100% |

Items 1 and 2 were added together and stirred for a minimum of 30 minutes at 70° C. using a 3-blade mixer at 200 RPM, until dissolution occurred, resulting in a colorless, transparent liquid fill. The temperature was reduced to 30° C. for encapsulation in an HPMC capsule (VCaps® Plus capsule, size 0, 50 capsules) followed by LEMS® automated sealing with a solution of isopropyl alcohol 75%/25% water. The filled capsules were then placed in 200 cc HDPE bottle in accelerated stability chamber at 40° C./75% RH. Capsules remained stable following 6 months exposure at accelerated conditions as shown in FIG. 1.

The filled capsules were also placed at room temperature, and remained stable for at least 6 months. Pharmacokinetic testing will be performed in humans with the filled capsules.

EXAMPLE 8

A formulation of the composition according to Table 7 was prepared:

TABLE 7

| Item # | Ingredient | Percent |
|---|---|---|
| 1 | HMB Free Acid | 60% |
| 2 | Fructose | 40% |
| | Total | 100% |

Items 1 and 2 were added together and stirred for a minimum of 30 minutes at 70° C. using a 3-blade mixer at 200 RPM, until dissolution occurred, resulting in a colorless, transparent liquid fill. The temperature was reduced to 30° C. for encapsulation in an HPMC capsule (VCaps® Plus capsule, size 0, 50 capsules) followed by LEMS® automated sealing with a solution of isopropyl alcohol 75%/25% water. The filled capsules were then placed in 200 cc HDPE bottle in accelerated stability chamber at 40° C./75% RH. Noticeable deterioration and softening of the capsule shell occurred after 2 weeks.

EXAMPLE 9

A formulation of the composition according to Table 8 was prepared:

TABLE 8

| Item # | Ingredient | Percent |
|---|---|---|
| 1 | HMB Free Acid | 57% |
| 2 | Beta Alanine | 43% |
| | Total | 100% |

Items 1 and 2 were added together and stirred for a minimum of 30 minutes at 70° C. using a 3-blade mixer at 200 RPM. The temperature was reduced to 30° C. for encapsulation in an HPMC capsule (VCaps® Plus capsule, size 0, 50 capsules) followed by LEMS® automated sealing with a solution of isopropyl alcohol 75%/25% water. The filled capsules were then placed in 200 cc HDPE bottle in accelerated stability chamber at 40° C./75% RH. Capsules remained stable following 6 months exposure at these accelerated conditions.

EXAMPLE 10

A formulation of the composition according to Table 9 was prepared:

TABLE 9

| Item # | Ingredient | Percent |
|---|---|---|
| 1 | HMB Free Acid | 72% |
| 2 | Choline Chloride | 28% |
| | Total | 100% |

Items 1 and 2 were added together and stirred for a minimum of 30 minutes at 70° C. using a 3-blade mixer at 200 RPM. The temperature was reduced to 30° C. for encapsulation in an HPMC capsule (VCaps® Plus capsule, size 0) followed by LEMS® automated sealing with a solution of isopropyl alcohol 75%/25% water. The filled capsules were then placed in 200 cc HDPE bottle in accelerated stability chamber at 40° C./75% RH. Capsules remained stable for at least 2 months after exposure at accelerated conditions until deterioration began thereafter.

EXAMPLE 11

A formulation of the composition according to Table 10 was prepared:

TABLE 10

| Item # | Ingredient | Percent |
| --- | --- | --- |
| 1 | HMB Free Acid | 57% |
| 2 | L-Arginine Ethyl Ester | 43% |
| | Total | 100% |

Items 1 and 2 were added together and stirred for a minimum of 30 minutes at 70° C. using a 3-blade mixer at 200 RPM. The temperature was reduced to 30° C. for encapsulation in an HPMC capsule (VCaps® Plus capsule, size 0, 50 capsules) followed by LEMS® automated sealing with a solution of isopropyl alcohol 75%/25% water. The filled capsules were then placed in 200 cc HDPE bottles in an accelerated stability chamber at 40° C./75% RH. Capsules remained stable for at least 2 months after exposure at accelerated conditions until deterioration began thereafter.

EXAMPLE 12

A formulation of the composition according to Table 11 will be prepared:

TABLE 11

| Item # | Ingredient | Percent |
| --- | --- | --- |
| 1 | HMB Free Acid | 40% |
| 2 | Fructose | 60% |
| | Total | 100% |

Items 1 and 2 will be added together and stirred for a minimum of 30 minutes at 70° C. using a 3-blade mixer at 200 RPM, until dissolution occurred, resulting in a colorless, transparent liquid fill. The temperature will be reduced to 30° C. for encapsulation in a size 00 HPMC capsule (VCaps® Plus capsule, 50 capsules) followed by LEMS® automated sealing with a solution of isopropyl alcohol 75%/25% water. The filled capsules will then be placed in 200 cc HDPE bottle in accelerated stability chamber at 40° C./75% RH and are expected to retain stability for at least six months.

EXAMPLE 13

Formulations according to the preceding Examples are made similarly, except the encapsulation is into an HPMC capsule with gellan gum (VCaps® capsules, any size) and LEMS® automated sealing is performed with a solution of isopropyl alcohol 80%/20% water and dried at 35° C. for approximately 3 minutes. Filled capsules will then be placed in 200 cc HDPE bottles in an accelerated stability chamber at 40° C./75% RH and are expected to retain stability for at least six months.

The invention claimed is:

1. A liquid filled hard capsule, comprising:
   a hard capsule shell comprising hydroxypropyl methyl cellulose; and
   a liquid fill inside the hard capsule shell comprising an effective amount of beta-hydroxy-beta-methylbutyric acid (HMB free acid) in liquid form and at least one excipient selected from quaternary ammonium salts, amino acids, amino acid derivatives, fructose, and/or any mixture thereof;
   wherein the excipient is present from about 30% w/w to about 60% w/w of the liquid fill and the liquid filled hard capsule is physically stable.

2. The liquid filled hard capsule according to claim 1, wherein the at least one excipient is choline chloride, L-carnitine base, beta-alanine, and/or any mixture thereof.

3. The liquid filled hard capsule according to claim 1, wherein the at least one excipient is choline chloride.

4. The liquid filled hard capsule according to claim 1, wherein the at least one excipient is a quaternary ammonium salt selected from L-carnitine base, L-carnitine HCl, acetyl-L-carnitine, L-carnitine tartrate, glycine propionyl-L-carnitine, and/or any mixture thereof.

5. The liquid filled hard capsule according to claim 1, wherein the at least one excipient is an amino acid selected from L-arginine ethyl ester HCl, beta alanine, L-isoleucine, HCl, L-leucine ethyl ester HCl, valine ethyl ester HCl, L-arginine ethyl ester HCl, and mixture thereof.

6. The liquid filled hard capsule according to claim 1, wherein the at least one excipient is present in an amount from about 35% w/w to about 40% w/w of the liquid fill.

7. The liquid filled hard capsule according to claim 1, further comprising at least one of a colorant, or a surfactant, or a viscosity modifying agent, or any mixture thereof.

8. The liquid filled hard capsule according to claim 1, wherein the liquid filled hard capsule is stable under conditions of 40° C./75% relative humidity for at least three months.

9. A process for manufacturing a liquid filled hard capsule, comprising:
   filling a hard capsule shell comprising hydroxypropyl methyl cellulose and having a cap and a body with a liquid fill to form a physically stable liquid filled hard capsule, wherein the liquid fill comprises an effective amount of beta-hydroxy-beta-methylbutyric acid (HMB free acid) in liquid form and at least one excipient selected from quaternary ammonium salts, amino acids, amino acid derivatives, fructose, and mixtures thereof, wherein said excipient is present from about 30% w/w to about 60% w/w of the liquid fill; and
   sealing or banding the liquid filled hard capsule where the cap and the body overlap.

10. A method, comprising administering the liquid filled hard capsule of claim 1 to a human or an animal, wherein the liquid filled hard capsule is banded.

11. A liquid filled hard capsule, comprising:
    a hard capsule shell comprising hydroxypropyl methyl cellulose; and
    a liquid fill inside the hard capsule shell comprising an effective amount of beta-hydroxy-beta-methylbutyric acid (HMB free acid) in liquid form and choline chloride in an amount ranging from about 30% w/w to about 60% w/w of the liquid fill; and
    wherein the liquid filled hard capsule is physically stable and is banded.

12. The liquid filled hard capsule according to claim 1, wherein the at least one excipient is present in an amount of about 40% to about 50% w/w of the liquid fill.

13. The liquid filled hard capsule according to claim 1, wherein the at least one excipient is present in an amount of about 38% w/w of the liquid fill.

14. The liquid filled hard capsule according to claim 1, wherein the liquid filled hard capsule is stable under conditions of 40° C./75% relative humidity for at least six months.

15. A method, comprising administering the liquid filled hard capsule of claim 1 to a human or an animal, wherein the liquid filled hard capsule is sealed.

16. The liquid filled hard capsule of claim 11, wherein the choline chloride is present in an amount ranging from about 40% to about 50% w/w of the liquid fill.

17. The liquid filled hard capsule of claim 11, wherein the liquid filled hard capsule is sealed.

18. A liquid filled hard capsule, comprising:
a hard capsule shell comprising hydroxypropyl methyl cellulose; and
a liquid fill inside the hard capsule shell comprising beta-hydroxy-beta-methylbutyric acid (HMB free acid) in liquid form in an amount of 40% w/w or more of the liquid fill, and at least one excipient selected from quaternary ammonium salts, amino acids, amino acid derivatives, fructose, and/or any mixture thereof;
wherein the excipient is present from about 30% w/w to about 60% w/w of the liquid fill and the liquid filled hard capsule is physically stable.

19. The process according to claim 9, wherein the at least one excipient is present in an amount of about 40% to about 50% w/w of the liquid fill.

* * * * *